United States Patent [19]

Mehlhorn et al.

[11] Patent Number: 5,188,832
[45] Date of Patent: Feb. 23, 1993

[54] AGENTS DIRECTED AGAINST PARASITES OF FISHES AND INSECTS

[75] Inventors: Heinz Mehlhorn, Neuss-Uedesheim; Horst Taraschewski; Günter Schmahl, both of Bochum; Wolfgang Raether, Dreieich; Manfred Rösner, Eppstein/Taunus, all of Fed. Rep. of Germany

[73] Assignee: Hoechst Aktiengesellschaft, Frankfurt am Main, Fed. Rep. of Germany

[21] Appl. No.: 480,158

[22] Filed: Feb. 14, 1990

[30] Foreign Application Priority Data

Feb. 16, 1989 [DE] Fed. Rep. of Germany ....... 3904593
Mar. 11, 1989 [DE] Fed. Rep. of Germany ....... 3908030

[51] Int. Cl.$^5$ .................... A01N 43/66; A01N 31/53
[52] U.S. Cl. .................................. 424/405; 514/241; 514/242; 514/243; 514/231.5; 544/83; 544/112; 544/180; 544/182; 544/220

[58] Field of Search ............... 424/405, 112; 544/180, 544/220, 182, 83; 514/242, 243, 241, 231.5

[56] References Cited

U.S. PATENT DOCUMENTS

| | | | |
|---|---|---|---|
| 4,631,278 | 12/1986 | Boeckx | 514/242 |
| 4,640,917 | 2/1987 | Rosner | 514/222 |
| 4,767,760 | 8/1988 | Boeckx | 514/242 |
| 4,778,887 | 10/1988 | Boeckx | 544/182 |
| 4,782,056 | 11/1988 | Rosner | 514/242 |

Primary Examiner—Thurman K. Page
Assistant Examiner—G. S. Kishore
Attorney, Agent, or Firm—Finnegan, Henderson, Farabow, Garrett and Dunner

[57] ABSTRACT

A method of using certain triazine-dione compounds for the control of endo- and ectoparasites of fish and/or insects. The compounds may be combined with aids to form an agent for controlling the endo- or ectoparasites.

11 Claims, No Drawings

AGENTS DIRECTED AGAINST PARASITES OF FISHES AND INSECTS

The invention relates to agents directed against parasitic protozoa and metazoa, some classes of which are widespread in fishes and insects.

Protozoa and metazoa are widespread parasites of livestock. Preferential attack by endoparasites is on internal organs and by ectoparasites is on the skin or eyes of the livestock, which may result in considerable damage.

In the case of fishes, parasitization by some protozoa and metazoa results in injury to the skin and gills, which makes the fishes susceptible to infections and/or kills them directly. Other such parasites attack internal organs of the fishes and frequently result in adhesions or the death of the fishes. In the large-scale management of fishes in large breeding facilities, parasitic protozoa and metazoa may rapidly spread throughout the stock and thus signify a great risk to the economic utilization of these facilities.

Parasitic protozoa and metazoa are likewise common among insects. In the case of the honey bee, protozoa such as Nosema apis are the cause of severe disease world-wide and may, besides reducing the production of honey, even result in the death of bee colonies. The parasites damage the hosts by destroying internal organs. Livestock weakened by this are often susceptible to other pathogens. Attack by Varroa mites weakens bees to such an extent that they often succumb to the Nosema pathogens.

Agents hitherto known for controlling parasitic protozoa and metazoa mostly have a spectrum of action which is too narrow. Moreover, the activity of some agents is too low so that it is necessary to administer high doses, which, on the other hand, increases the risk of toxic effects For the said reasons, and because of the possible development of resistance to available agents, there is a continuous need for new and effective agents directed against parasites of fishes and insects.

The invention relates to the use of compounds of the general formula (I)

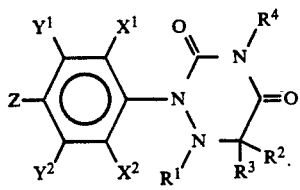

in which $R^1$ represents together with $R^2$ a chemical bond or hydrogen, straight-chain or branched $C_1$-$C_{12}$-alkyl, $C_3$-$C_8$-cycloalkyl, benzyl which can be substituted in the phenyl ring by 1–3 radicals from the group comprising halogen and $C_1$-$C_4$-alkyl, or $C_1$-$C_{12}$-alkanoyl which can be substituted 1 to 3 times by halogen, or benzoyl which can be substituted by 1 to 3 radicals from the group comprising halogen and $C_1$-$C_4$-alkyl, $R^2$ represents together with R a chemical bond or hydrogen, $R^3$ represents hydrogen, $C_1$-$C_{12}$-alkyl or $C_3$-$C_8$-cycloalkyl, $R^4$ represents hydrogen, straight-chain or branched $C_1$-$C_{12}$-alkyl, $C_3$-$C_8$-cycloalkyl, benzyl which can be substituted by 1 to 3 radicals from the group comprising halogen and $C_1$-$C_4$-alkyl, $X^1$, $X^2$, $Y^1$, $Y^2$ and Z represent, independently of one another, a) hydrogen, halogen, trifluoromethyl, $C_1$-$C_6$-alkyl, $C_3$-$C_6$-cycloalkyl, $C_1$-$C_6$-alkoxy, $C_1$-$C_6$-alkylthio, $C_1$-$C_6$-alkylsulfinyl, $C_1$-$C_6$-alkylsulfonyl, benzylthio, benzylsulfinyl, benzylsulfonyl, nitro, cyano, amino, $C_1$-$C_{12}$-alkylamino, di-($C_1$-$C_{12}$-alkyl)-amino, N-($C_1$-$C_{12}$-alkyl)-aminomethyl, N,N-di-($C_1$-$C_{12}$-alkyl)-aminomethyl, piperidino, morpholino, thiomorpholino, 1-pyrrolidinyl, 4-methyl-1-piperazinyl or $C_1$-$C_6$-acylamino or b) a phenoxy, phenylthio, phenylsulfinyl, phenylsulfonyl, benzoyl, benzoylamino, phenylamino, N,N-phenyl-($C_1$-$C_6$-alkyl)-amino, 1-cyano-1-phenyl-methyl, 1-cyano-1,1-diphenyl-methyl,1-cyano-1-phenyl-1-($C_3$-$C_6$-cycloalkyl)-methyl, 1-cyano-1-phenyl-1-($C_3$-$C_6$-cycloalkyl)-methyl, thienyl or naphthyl radical, each of which is unsubstituted or substituted a total of 1, 2 or 3 times in the phenyl ring by radicals mentioned under a), for controlling endo- and ectoparasites of fishes and insects.

Of particular interest is the use of compounds of the general formula (I) in which $X^1$, $X^2$, $Y^1$, $Y^2$ are selected, independently of one another, from the group of radicals comprising hydrogen, halogen, in particular chlorine, trifluoromethyl, $C_1$-$C_4$-alkyl, $C_1$-$C_4$-alkoxy, nitro and cyano.

Preferably used are compounds of the general formula (I) in which $X^1$ and $X^2$ represent, independently of one another, hydrogen or $C_1$-$C_4$-alkyl, preferably hydrogen or methyl, in particular only hydrogen, and $Y^1$ and $Y^2$ are selected, independently of one another, from the group of radicals comprising hydrogen, halogen, in particular chlorine, trifluoromethyl, $C_1$-$C_4$-alkyl, in particular methyl and ethyl.

Preferably employed are compounds of the general formula (I), according to the invention, in which Z represents a) hydrogen, $C_1$-$C_4$-alkoxy, $C_1$-$C_4$-alkylthio, $C_1$-$C_4$-alkylsulfinyl, $C_1$-$C_4$-alkylsulfonyl, benzylthio, benzylsulfinyl or benzylsulfonyl, or b) phenoxy, phenylthio, phenylsulfinyl, phenylsulfonyl, benzoyl, benzoylamino, phenylamino, 1-cyano-1-phenyl-methyl, 1-cyano-1-phenyl-1-($C_1$-$C_6$-alkyl)-methyl, thienyl or a radical which is mentioned under b) and is substituted by 1 to 3 radicals from the group comprising c) halogen, in particular chlorine, trifluoromethyl, $C_1$-$C_6$-alkyl, $C_1$-$C_6$-alkoxy, $C_3$-$C_6$-cycloalkyl, $C_1$-$C_4$-alkylthio, $C_1$-$C_4$-alkylsulfinyl, $C_1$-$C_4$-alkylsulfonyl, nitro, cyano, amino, $C_1C_4$-alkylamino, N,N-di-($C_1$-$C_4$-alkyl)-amino and $C_1$-$C_4$-acylamino.

Particularly preferred is the use of the compounds of the general formula (I) in which Z represents phenoxy, phenylthio, phenylsulfinyl, phenylsulfonyl, 1-cyano-1-phenyl-methyl or one of the said radicals which is substituted by 1 or 2 substituents from the group comprising halogen, in particular chlorine, trifluoromethyl, $C_1$-$C_4$alkyl, $C_1$-$C_4$-alkoxy, $C_1$-$C_4$-alkylthio, $C_1$-$C_4$-alkylsulfinyl and $C_1$-$C_4$-alkylsulfonyl.

In the compounds of the general formula (I) $R^1$ is preferably together with $R^2$ a chemical bond or hydrogen, straight-chain or branched $C_1$-$C_4$-alkyl, in particular methyl or ethyl, benzyl, $C_1-C_5$-alkanoyl or benzoyl;

$R^2$ is preferably hydrogen or together with $R^1$ a chemical bond;

$R^3$ is preferably hydrogen or $C_1-C_4$-alkyl, in particular methyl or ethyl;

$R^4$ is preferably hydrogen, straight-chain or branched $C_1-C_4$-alkyl, in particular methyl or ethyl, or benzyl.

In the case where $R^4=H$, the compounds of the formula (I) can be in the form of salts. The invention also relates in particular to the physiologically tolerated salts of the compound of the formula (I), for example the alkali, metal, alkaline earth metal or optionally substituted ammonium salts.

Particularly preferred compounds of the said formula (I) are those which contain a combination of the above-mentioned preferred features.

The compounds of the formula (I) which are used according to the invention are, as a rule, known or can be prepared in an analogy to known processes; see, for example, EP-A-0215 354, EP-A-0154 885, EP-A-0170 316, EP-A-0232 932, DE-A-27 22 537 and DE-A-24 23 972.

Examples of suitable compounds for the use according to the invention are

2-[3,5-Dichloro-4-(4-methylsulfonyl-phenoxy)-phenyl]-1-methyl-hexahydro-1,2,4-triazine-3,5-dione, 2-[3,5-Dichloro-4-(4-methylthiophenoxy)-phenyl]-1-methylhexahydro-1,2,4-triazine-3,5-dione, 2-[3,5-Dichloro-4-(4-methylsulfinylphenoxy)-phenyl]-1-methyl-hexahydro-1,2,4-triazine-3,5-dione, 2-[3,5-Dichloro-4-(3-methyl-4-methylthio)-phenyl]-1-methyl-hexahydro-1,2,4-triazine-3,5-dione, 2-[3,5-Dichloro-4-(4-chlorophenylthio)-phenyl]-1-methylhexahydro-1,2,4-triazine-3,5-dione, 2-[3,5-Dichloro-4-(4-methylthio-phenoxy)-phenyl]-hexahydro-1,2,4-triazine-3,5-dione, 2-[3,5-Dichloro-4-(4-methylsulfinyl-phenoxy)-phenyl]-hexahydro-1,2,4-triazine-3,5-dione, 2-[3,5-Dimethyl-4-(4-methylthio-phenoxy)-phenyl]-hexahydro-1,2,4-triazine-3,5-dione, 2-[3,5-Dichloro-4-(3-methyl-4-methylthio-phenoxy)-phenyl]-hexahydro-1,2,4-triazine-3,5-dione, 2-[3,5-Dichloro-4-(4-chlorophenylthio)-phenyl]-hexahydro-1,2,4-triazine,3,5-dione, 2-[3,5-Dichloro-4-(4-methylthio-phenylthio)-phenyl]-hexahydro-1,2,4-triazine,3,5-dione, 2-[3,5-Dichloro-4-(4-methylsulfonyl-phenoxy)-phenyl]-hexahydro-1,2,4-triazine-3,5-dione, 2-[3,5-Dichloro-4-(4-methylsulfonylphenoxy)-phenyl]-1,2,4-triazine-3,5-(2H,4H)-dione, 2-[3,5-Dichloro-4-(4-methylthio-phenoxy)-phenyl]-1,2,4-triazine-3,5-(2H,4H)-dione, 2-[3,5-Dichloro-4-(4-methylsulfinyl-phenoxy)-phenyl]-1,2,4-triazine-3,5-(2H,4H)-dione, 2-[3,5-Dichloro-4-(3-methyl-4-methylthio-phenoxy)-phenyl]-1,2,4-triazine-3,5-(2H,4H)-dione, 2-[3,5-Dichloro-4-(4-chlorophenylthio)-phenyl]-1,2,4-triazine-3,5-(2H,4H)-dione, 2-[3,5-Dichloro-4-(1-cyano-1-(4-chlorophenyl)-methyl)-phenyl]-1,2,4-triazine-3,5-(2H,4H)-dione and 2-[3-Chloro-4-(1-cyano-1-(4-chlorophenyl)-methyl)-phenyl]-1,2,4-triazine-3,5-(2H,4H)-dione.

The known compounds have been described as agents for controlling coccidiosis, in particular in poultry management (see abovementioned literature). It was surprising that they can be employed effectively against parasites in fishes and insects.

Examples of parasites which can be effectively controlled with compounds of the formula (I) are fish parasites from the phylum of protozoa and metazoa, in particular protozoa from the class Ciliata, such as *Ichthyophthirius multifiliis*, *Chilodonella cyprini*, Trichodina spp., Glossatella spp., Apiosoma spp., Epistylis spp., or from the class Myxozoa, such as *Myxobolis cerebralis*, Myxosoma spp., Myxidium spp., Myxobolus spp., Henneguya spp. and Hoferellus or of the class of Microsporidia such as Glugea spp., Thelohania spp., and Pleistophora spp., or platyhelminths of the class Monogenea, such as Dactylogyrus spp., Gyrodactylus spp., Pseudodactylogyrus spp., Diplozoon spp. etc. Additional possible parasites of fishes are amebae, intestinal flagellates and coccidia. Examples of parasites of insects, in particular bees and silkworms, are amebae, Microsporidia such as *Nosema apis* in bees, mites of the Acarapis species and brood mites of the class Varroa.

The preferred use is for the treatment of fishes against parasites of the skin and the gills.

The compounds of the formula (I) are suitable for the treatment of both fresh water and salt water fishes. For example, it is possible to treat productive, breeding, aquarium and ornamental fishes of a wide variety of ages, in particular ornamental or breeding fishes such as salmon, roach, carp, trout, eel, bream, whitefish, plaice, halibut, sole, chub, seabream (Dicentrarchus spp.), red seabream (*Pagurus major*), gray mullet (*Mugil cephalus*), pompano, gilthead seabream (*Sparus auratus*), Tilapia spp., Japanese eel (*Anguilla japonica*), yellow tail (*Seriola quinqueradiata*) and chichlid species such as Plagioscion and channel catfish.

The use according to the invention is particularly suitable for the treatment of fish fry, for example of carp, eel and ornamental fishes.

The treatment of the fishes with a compound of the formula (I) can take place, for example, by adding the compound or an agent which contains the compound to the water in which the fishes are kept. For example, the fishes can be placed in a bath or trough and treated for a relatively short time, for example from minutes up to several hours. A treatment of this type is easy to carry out in breeding facilities when transferring the fishes from one breeding trough into another. An alternative possibility is longer-lasting treatment of the habitat of the fishes, for example in aquaria, fish troughs, tanks or ponds. It is likewise possible to administer the compounds of the formula (I) to the fishes orally, for example in the feed.

The treatment of the fishes can also be carried out in combination with other active substances, for example those which are preferentially active against other pests.

The insects include the productive and breeding insects kept by people, such as, for example honey bees, silkworms, parasitic wasps; also included are insects which are bred for experimental purposes or kept for collecting genetic material. The compounds of the formula (I) are suitable for the treatment of all stages of development of the insects.

A treatment in combination with other active substances is possible, for example a treatment of bees against *Nosema apis* and *Varroa jacobsoni* with a compound of the formula (I) and with one or more active substances from the group comprising synthetic phosphoric esters such as coumaphos and malathion, pyrethroids such as flumethrin, cyfluthrin and cyalothrin, amitraz and cymiazol, formamidines such as chlordimeform and phenothiazines such as promazine.

The insects can be treated, for example by feeding or contacting the insects with finely divided active substance, where appropriate in combination with auxiliaries. For this purpose, the active substance is, for example, sprayed, atomized, vaporized, nebulized, used to fumigate or applied dispersed in or on vehicles.

Treatment can also take place systemically via the hemolymph of the insects, in which case the active substance is preferably added to the feed or drinking water or offered in an appropriate manner.

The insects can be treated throughout the year, in the case of honey bees preferably at the winter feeding-down and/or in the brood-free period.

As a rule, the active compounds are formulated in a particular manner appropriate for the use. The invention therefore also relates to agents containing compounds of the said formula (I), for controlling endo- and ectoparasites of fishes and insects.

Suitable agents for the short-term or prolonged treatment of the fishes in baths or ponds are solutions of the active substances in one or more polar solvents, and the solution ought as a rule to have an alkaline reaction on dilution with water. Agents of this type can be prepared, for example, by dissolving the active substance in a water-soluble solvent which either itself has an alkaline reaction or is treated with a water-soluble base. The base can be dissolved or suspended in the agent. On dilution of the agent with water to the use concentration, the pH which is set up ought preferably to be from 7 to 10, in particular from 8 to 10. Suitable for preparing agents in solution form are water-soluble solvents in which the active substance is soluble in adequate concentration, preferably 0.4 to 60% by weight, in particular 1 to 30% by weight, and which are physiologically acceptable. Examples of suitable solvents are alcohols such as ethanol and isopropanol, aromatic alcohols such as benzyl alcohol, polyhydroxy compounds such as glycerol, propylene glycol, polyethylene glycols, block polymers of ethylene oxide and propylene oxide, aminoalkanols such as ethanolamine, diethanolamine, triethanolamine, ketones such as acetone, and methyl ethyl ketone, esters such as ethyl acetate or dispersing and emulsifying agents such as polyethylene glycol ethers, polyethylene glycol alkylamines, polyethylene glycol stearate, nonylphenol polyethylene glycol ethers, polyoxyethylene sorbitan monooleate or polyethoxylated castor oil.

Suitable for setting out the alkaline medium are bases such as, for example, organic bases from the group of amino acids, specifically L- or D,L-arginine and L- or D,L-lysine, or glucosamine, methylglucosamine, 2-amino-2-hydroxymethyl-1,3-propanediol or else N,N,N',N'-tetrakis-(2-hydroxypropyl)-ethylenediamine; likewise suitable are inorganic bases such as ammonia or sodium carbonate.

The agents according to the invention in solution form can also contain other formulating substances, preferably 0.1 to 20% by weight of auxiliaries from the group of antioxidants, surfactants, suspension stabilizers and thickening agents such as methylcellulose, alginates, polysaccharides, galactomannans or colloidal silica. Builders for livestock nutrition, flavorings and colorants can likewise be added. In many cases, acids which form a buffer system with the base content are also suitable for setting out the pH of the solution.

Agents for oral use can be powders, granules, solutions, emulsion or suspension concentrates, which are as a rule administered in a homogeneous mixture with the feed. Agents of these types can be prepared in analogy to customary processes, for example by mixing the active substance with solid or liquid vehicles and possibly with the addition of emulsifying or dispersing agents, solubilizers, colorants, preservatives and/or antioxidants.

Examples of solid vehicles which may be mentioned are natural rock powders such as kaolins, aluminas, talc, chalk, diatomaceous earth, organic vehicles such as sucrose, lactose, glucose, fine or coarse cereals meals, starch, animal meals, cellulose, milk powder, inorganic vehicles such as sodium chloride, carbonates such as calcium carbonate or bicarbonates, aluminum oxides, silica and silicates. Examples of suitable liquid vehicles and solubilizers are water, alcohols such as ethanol or isopropanol, glycols such as ethylene glycol, propylene glycol, polyethylene glycols, polypropylene glycols, block polymers of propylene oxide and ethylene oxide, glycerol, aromatic alcohols such as benzyl alcohol, phenylethylethanol and phenoxyethanol, esters such as ethyl acetate, butyl acetate and benzyl benzoate, alkylene glycol alkyl ethers such as dipropylene glycol monomethyl ether, diethylene glycol monobutyl ether, ketones such as acetone and methyl ethyl ketone, aromatic and aliphatic hydrocarbons, vegetable and synthetic oils, dimethylformamide, dimethyl sulfoxide, dimethylacetamide and N-methylpyrrolidone.

Examples of suitable dispersing and emulsifying agents are non-ionic surfactants such as polyethoxylated castor oil, polyoxyethylene sorbitan monooleate, sorbitan stearate, ethanol glycerol monostearate, polyethylene glycol stearate, alkylphenol polyglycol ethers such as nonylphenol polyglycol ether, ampholytic surfactants such as disodium N-lauryl-$\beta$-iminodipropionate or lecithin, anionic surfactants such as sodium lauryl sulfate, fatty alcohol ether sulfates and cationic surfactants such as cetyltrimethylammonium chloride. The concentration of the active substance in agents for oral use can vary within wide limits and is preferably between 0.0001 and 15% by weight. Feed additives according to the invention are composed, for example, of 1 to 10% by weight of the compound of the formula (I) and 49–90% by weight of soybean protein or of 0.5 to 10% by weight of compound of the formula (I), 0.05 to 1.5% by weight of benzyl alcohol, up to 4% hydroxypropylmethylcellulose and the remainder of water.

The effective dose of compound of the formula (I) for the treatment of the fishes depends on the nature and duration of the treatment as well as the age and condition of the treated fishes. The dose on treatment in baths is as a rule between 0.1 and 50 mg of active substance per liter of water. On treatment for a shorter time, the concentration is preferably 2 to 50 mg of active substance per liter, in particular 5 to 10 mg of active substance per liter, of water with a treatment time of 1 to 5 hours. The concentration is as a rule lower for younger fishes than for older fishes. When the treatment times are longer, the concentration can likewise as a rule be set at a lower level. On long-term treatment of the habitat of the fishes, for example in ponds, preferably 0.1 to 5 mg of active substance are used per liter of water.

Suitable agents for the spray treatment of insects contain the active substance in a concentration of 0.1 to 50% by weight, preferably 0.3 to 20% by weight, in addition to diluents and/or auxiliaries, such as emulsifiers, which are tolerated by the insects at the concentrations used. When administered in the feed, a saturated sugar solution is preferably used as vehicle.

Examples of suitable diluents are water, alcohols such as methanol, ethanol, n- and i-propanol, butanol, pentanol, hexanol, heptanol and octanol, glycerol, glycols such as ethylene glycol, propylene glycol, 1,3- and 1,4-butylene glycol as well as appropriate glycol monomethyl or dimethyl ethers, or benzyl alcohol and related aromatic alcohols, esters such as ethyl, propyl or butyl acetate, ethyl lactate, ketones such as acetone and methyl ethyl ketone, mono- and triglycerides with natural or fatty acids, vegetable and synthetic oils, for example castor oil, olive oil, liquid aliphatic hydrocarbons, dimethyl sulfoxide, dimethylacetamide, dimethylformamide and N-methylpyrrolidone.

Suitable emulsifiers are anionic, cationic, non-ionic and ampholytic surfactants. Examples of emulsifiers are fatty alcohol sulfates and ether sulfates, for example sodium lauryl sulfate, alkylarylsulfonates, tetraalkylammonium salts such as cetyltrimethylammonium chloride, lecithin, di-Na N-lauryl-$\beta$-iminodipropionate, polyethoxylated castor oil, sorbitan fatty acid esters, polyethoxylated sorbitan fatty acid esters, fatty acid polyglycol ethers, alkylphenol polyglycol ethers.

The agents for the spray treatment of the insects contain the emulsifiers and the active substance preferably in the ratio of 0.05 to 10:1, in particular 0.1 to 5:1, by weight and are prepared by dissolving the active substances in the diluent and/or emulsifier, adding the other components and auxiliaries and, where appropriate, further diluting with water to the desired concentration. The agents can be sprayed in relatively high concentration by the ULV process (ultra low-volume process) with equipment suitable for this purpose or by means of electrostatic charging. Conventionally, the sprayable agents are as a rule diluted to concentrations of $10^{-4}$ to 5% by weight of active substance, preferably $10^{-3}$ to 0.5% by weight of active substance, with water and sprayed with conventional equipment such as knapsack sprayer, piston pump or paint spray.

Suitable dusting agents for treating insects contain, besides the active substance, vehicles which are tolerated by the insects and are suitable for preparing dusting powders and wettable powders, as well as, where appropriate, wetting agents which correspond to the emulsifiers listed above. Examples of inorganic vehicles are talc, kaolin, calcium carbonate, silicates, bentonite; organic vehicles which may be mentioned are starches such as rice starch, sugars, cellulose and derivatives thereof. The agents are prepared by intimately mixing the components.

Other agents and aids for treating insects where the active substances are vaporized, atomized or used to fumigate can be prepared with compounds of the formula (I), and used, by methods customary for treating insects.

Insect-treating agents which have a systemic action contain besides preferably 0.5 to 25%, preferably 1 to 10%, by weight of active substances of the formula (I) feedstuffs such as types of sugars in the form of granules, solutions, suspensions, emulsions or other mixtures. The mixtures are as a rule diluted with water or sugar solution to use concentrations of, preferably, $10^{-9}$ to 2% by weight, in particular $10^{-4}$ to 0.1% by weight, or are in the form of solid feed pastes or mixtures which are ready for use and contain the active substance in the use concentration, in addition to sugar and starch. Agents which have a systemic action and can, as water-miscible solutions of the active substances, be added to the drinking water of the insects are preferred. These agents preferably contain auxiliaries such as emulsifiers and solvents as are also suitable for the abovementioned agents for the treatment of fishes in baths and ponds, in particular the agents for controlling the pH. The solution of the active substance concentrate should preferably not exceed a pH of 11. To prepare the agents having a systemic action, in a straightforward manner the active substances are mixed with the solvent and emulsifier until a clear solution has been produced.

EXAMPLE 1

In vivo tests on carp

Carp in the breeding stage of 6–8 cm which were heavily infected with ectoparasites from the class of Monogenea (25–42 Monogenea of the species Dactylogyrus vastator and Dactylogyrus extensus per fish) or Ciliata (several hundred trophozoites of the species *Ichthyophthirius multifiliis* per fish) were treated with 2-[3,5-dichloro-4-(4-methylsulfonyl-phenoxy)-phenyl]-1-methylhexahydro-1,2,4-triazine-3,5-dione at the stated concentration in short-term baths at 22° C. with aeration, and were examined after various incubation times. The results are compiled in Table 1.

At the concentrations used the fishes showed no intolerance of the active substance.

TABLE 1

| Test no. | Active substance concentration (mg/ml) | Incubation time | Efficacy for D. vastator and D. extensus | I. multifiliis |
|---|---|---|---|---|
| 1 | 1 | 2 h | efficacy low, a few dead worms | ineffective |
| 2 | 1 | 3 h | efficacy low, a few dead worms | ineffective |
| 3 | 5 | 1 h | 30% dead worms, 30% with reduced motility, 40% normal | ineffective |
| 4 | 5 | 2 h | 90% dead worms, 10% reduced motility; | ineffective |
| 5 | 5 | 3 h | 90% dead worms, 10% reduced motility; | ineffective |
| 6 | 10 | 1 h | 100% dead worms | ineffective |
| 7 | 10 | 2 h | 100% dead worms | few dead trophozoites (sediment) |
| 8 | 10 | 3 h | 100% dead worms | somewhat greater effect than in Test 7 |
| 9 | 10 | 4 h | 100% dead worms | Fishes free of symptoms |
| 10 | 15 | 1 h | 100% dead worms | Ineffective |
| 11 | 15 | 2 h | 100% dead worms | Few dead trophozoites |
| 12 | 15 | 3 h | 100% dead worms | 80% dead trophozoites |

EXAMPLE 2

In vitro incubation of trophozoites (*Ichthyophthirius multifiliis*) from carp gills or eel gills Trophozoites 150 to 900 μm in size, which were kept in water, were adjusted to a concentration of 50 trophozoites/100 ml of water in Boveri dishes to which 2-3,5-dichloro-4-(4-methylsulfonyl-phenoxy)-phenyl]-1-methyl-hexahydro-1,2,4-triazine-3,5-dione was added in the stated concentration; temperature 20° C. The results are compiled in Table 2.

TABLE 2

| Test no. | Active substance concentration (mg/ml) | Incubation time | Effect |
|---|---|---|---|
| 1 | 5 | 1 h | 100% cytolysis |
| 2 | 10 | 1 h | 100% cytolysis |
| 3 | 15 | 1 h | 100% cytolysis |
| 4 | 10 | 15 min | 100% cytolysis |
| 5 (control) | 0 | 12 | no cytolysis; tomite formation |

EXAMPLE 3

In vivo tests on ornamental fishes

Groups of 10 ornamental fishes of the species neon red (*Paracheirodon axelrodi*, 18–25 mm), swordtails (*Xiphophorus helleri*) and zebra fishes (*Brachydanio rerio*, 30–32 mm) were treated with 10 mg/l 2-[3,5-dichloro-4-(4-methylsulfonyl-phenoxy)-phenyl]-1-methylhexahydro-1,2,4-triazine-3,5-dione, which was added directly to the bath water, in short-term baths at 25° C. with aeration, and thus the tolerability was tested. Fishes infected with *Ichthyophthirius multifiliis* were treated under analogous conditions. The results are compiled in Table 3.

TABLE 3

| Test no. | Fish species | Infected | Treatment time | Parasites per fish | Effect on parasites | Tolerability |
|---|---|---|---|---|---|---|
| 1 | Neon red | no | 4 h | — | — | 100% |
| 2 | | yes | 4 h | a few trophozoites still on the fishes | many dead trophozoites at the bottom | 100% |
| 3 | Swordtail | no | 4 h | — | — | 100% |
| 4 | Swordtail | yes | 4 h | a few trophozoites still on the fishes | many dead trophozoites at the bottom; fishes free of symptoms after 4 days | 100% |
| 5 | Zebra fish | no | 4 h | — | — | 100% |
| 6 | Zebra fish | yes | 4 h | a few trophozoites on the fishes | many trophozoites at the bottom | |

EXAMPLE 4

In vivo treatment of sticklebacks

The efficacy of 10 mg/l 2-]3,5-dichloro-4-(4-methylsulfonyl-phenoxy)-phenyl[-1-methyl-hexahydro-1,2,4-triazine-3,5-dione against parasites was investigated on a relatively large number of infected sticklebacks which were infected with the Monogenea, Ciliata and Microsporidia species indicated in Table 4 (see Table 4).

TABLE 4

| Test no. | Infection by | Incubation time | Effects on fish | Effects on parasites |
|---|---|---|---|---|
| 1 | *Gyrodactylus arcuatus* | 1 h | no worms on fish | dead worms in sediment |
| 2 | *Gyrodactylus arcuatus* | 4 h | no worms on fish | lysed worms no longer detectible |
| 3 | *Trichodina* spp. | 4 h | fishes 100% parasite-free | all parasites killed |
| 4 | *Glugea anomala* | 4 h | fishes 100% parasite-free | meronts and sporoblasts completely destroyed |

EXAMPLE 5

In vitro treatment of Monogenea

Monogenea of the species *Pseudodactylogyrus bini* kept in water were treated in analogy to Example 2 at a concentration of 10 mg/l of the same active substance. 90% of the worms had been killed after only 2¼ hours.

EXAMPLE 6

In analogy to Example 1 the efficacy of 2-[3,5-dichloro-4-(1-cyano-1-(4-chlorophenyl)-methyl)-phenyl]-1,2,4-triazine-3,5-(2H,4H)-dione against protozoa (*Trichodina* sp.; *Apiosoma* sp.) and Monogenea (*Gyrodactylus arcuatus*) was tested on carp and sticklebacks (see Table 5).

TABLE 5

| Test no. | Infection by | Concentration (mg/l)/time (h) | Effects on parasites on carp and sticklebacks |
|---|---|---|---|
| 1 | *Trichodina* sp. | 10/1 | 100% lethal |
| 2 | *Apiosoma* sp. | 10/1 | 100% lethal |
| 3 | *Gyrodactylus arcuatus* | 5/1 | 100% lethal |

EXAMPLE 7

Example 6 was repeated but with 2-[3-chloro-4-(1-cyano-1-(4-chlorophenyl)-methyl)-phenyl]-1,2,4-triazine-3,5-(2H,4H)-dione being employed as active substance. Correspondingly good results were obtained.

We claim:

1. A method which comprises treating insects or productive, breeding, aquarium or ornamental fishes infested with parasitic protozoa or metazoa by administering an effective amount of a compound of the formula (I)

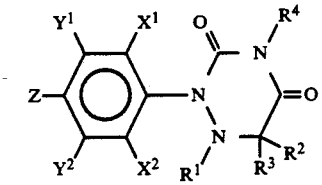

in which

R¹ represents together with R² a chemical bond or hydrogen, straight-chain or branched $C_1$–$C_{12}$-alkyl, $C_3$–$C_8$-cycloalkyl, benzyl which can be substituted in the phenyl ring by 1–3 radicals from the group comprising halogen and $C_1$–$C_4$-alkyl, or $C_1$–$C_{12}$-alkanoyl which can be substituted 1 to 3 times by halogen, or benzoyl which can be substituted by 1 to 3 radicals from the group comprising halogen and $C_1$–$C_4$-alkyl, R² represents together with R¹ a chemical bond or hydrogen, R³ represents hydrogen, $C_1-C_{12}$-alkyl or $C_3-C_8$-cycloalkyl,
$R^4$ represents hydrogen, straight-chain or branched $C_1-C_{12}$-alkyl, $C_3-C_8$-cycloalkyl, benzyl which can be substituted by 1 to 3 radicals from the group comprising halogen and $C_1-C_4$-alkyl, $X^1$, $X^2$, $Y^1$, $Y^2$ and Z represent, independently of one another,
a) hydrogen, halogen, trifluoromethyl, $C_1-C_6$-alkyl, $C_3-C_6$-cycloalkyl, $C_1-C_6$-alkoxy, $C_1-C_6$-alkylthio, $C_1-C_6$-alkylsulfinyl, $C_1-C_6$-alkylsulfonyl, benzylthio, benzylsulfinyl, benzylsulfonyl, nitro, cyano, amino, $C_1-C_{12}$-alkylamino, di-($C_1-C_{12}$-alkyl)-amino, N-($C_1-C_{12}$-alkyl)-aminomethyl, N,N-di-($C_1-C_{12}$-alkyl)-aminomethyl, piperidino, morpholino, thiomorpholino, 1-pyrrolidinyl, 4-methyl-1-piperazinyl or $C_1-C_6$-acylamino or
b) a phenoxy, phenylthio, phenylsulfinyl, phenylsulfonyl, benzoyl, benzoylamino, phenylamnio, N,N-phenyl-($C_1-C_6$-alkyl)-amino, 1-cyano-1-phenyl-methyl, 1-cyano-1,1-diphenylmethyl, 1-cyano-1-phenyl-1-($C_1-C_6$-alkyl)-methyl, 1-cyano-1-phenyl-1-($C_3-C_6$-cycloalkyl)-methyl, thienyl or naphthyl radical, each of which is unsubstituted or substituted a total of 1, 2 or 3 times in the phenyl ring by radicals mentioned under a), or else their physiologically tolerated salts in the case where $R^4$=H, by causing said fishes or insects to ingest said compound, or by introducing said compound into the habitat the fishes or insects, or by contacting the insects with the compound.

2. The method of claim 1, wherein $X^1$, $X^2$, $Y^1$, $Y^2$ are selected, independently of one another, from the group of radicals comprising hydrogen, halogen, in particular chlorine, trifluoromethyl, $C_1-C_4$-alkyl, $C_1-C_4$-alkoxy, nitro and cyano.

3. The method of claim 1, wherein $X^1$ and $X^2$ represent, independently of one another, hydrogen or $C_1-C_4$-alkyl, preferably hydrogen or methyl, in particular only hydrogen, and $Y^1$ and $Y^2$ are selected, independently of one another, from the group of radicals comprising hydrogen, halogen, in particular chlorine, trifluoromethyl, $C^1-C_4$-alkyl, in particular methyl and ethyl.

4. The method of claim 1, wherein Z represents
a) hydrogen, $C_1-C_4$-alkoxy, $C_1-C_4$-alkylthio, $C_1-C_4$-alkylsulfinyl, $C_1-C_4$-alkylsulfonyl, benzylthio, benzylsulfinyl or benzylsulfonyl, or
b) phenoxy, phenylthio, phenylsulfinyl, phenylsulfonyl, benzoyl, benzoylamino, phenylamino, 1-cyano-1-phenyl-methyl, 1-cyano-1-phenyl-1-($C_1-C_6$-alkyl)-methyl, thienyl or a radical which is mentioned under b) and is substituted by 1 to 3 radicals from the group comprising
c) halogen, in particular chlorine, trifluoromethyl, $C_1-C_6$-alkyl, $C_1-C_6$-alkoxy, $C_3-C_6$-cycloalkyl, $C_1-C_4$-alkylsulfinyl, $C_1-C_4$-alkylsulfonyl, nitro, cyano, amino, $C_1-C_4$-alkylamino, N,N-di-($C_1-C_4$-alkyl)-amino and $C_1-C_4$-acylamino.

5. The method of claim 1, where Z represents phenoxy, phenylthio, phenylsulfinyl, phenylsulfonyl, 1-cyano-1-phenyl-methyl or one of the said radicals which is substituted by 1 or 2 substituents from the group comprising halogen, in particular chlorine, trifluoromethyl, $C_1-C_4$-alkyl, $C_1-C_4$-alkoxy, $C_1-C_4$-alkylthio, $C_1-C_4$-alkylsulfinyl and $C_1-C_4$-alkylsulfonyl.

6. The use as claimed in claim 1, wherein
$R^1$ denotes together with $R^2$ a chemical bond or alone denotes hydrogen, straight-chain or branched $C_1-C_4$-alkyl, in particular methyl or ethyl, benzyl, $C_1-C_5$-alkanoyl or benzoyl;
$R^3$ denotes hydrogen or $C_1-C_4$-alkyl, in particular methyl or ethyl;
$R^4$ denotes hydrogen, straight-chain or branched $C_1-C_4$-alkyl, in particular methyl or ethyl, or benzyl.

7. The method of claim 1 for controlling fish parasites, wherein the water in which the fishes are located contains 0.1 to 50 mg of compound of the formula (I) per liter of water.

8. The method of claim 1, wherein said compound is 2-[3,5-dichloro-4-(4-methylsulfonyl-phenoxy)-phenyl]-1-methylhexahydro-1,2,4-triazine-3,5-dione.

9. The method of claim 1, wherein said fishes are selected from salmon, roach, carp, trout, eel, bream, whitefish, plaice, halibut, sole, chub, seabream, red seabream, gray mullet, pompano, gilthead seabream, Tilatia spp., Japanese eel, yellow tail and chiclid species.

10. The method of claim 1, wherein said insects are selected from honeybees, silkworms, parasitic wasps and insects which are bred for experimental purposes or kept for collecting genetic material.

11. The method of claim 1, wherein said parasitic protozoa or metazoa are selected from Ciliata, Myxozoa, Microsporidia, Monogenea, amoebae, intestinal flagellates, Coccidia, mites and brood mites.

* * * * *

UNITED STATES PATENT AND TRADEMARK OFFICE
CERTIFICATE OF CORRECTION

PATENT NO.    :   5,188,832
DATED         :   February 23, 1993
INVENTOR(S)   :   Heinz Mehlhorn et al.

It is certified that error appears in the above-identified patent and that said Letters Patent is hereby corrected as shown below:

Claim 1, column 11, line 18, change "phenylamnio" to --phenylamino--.

Claim 1, column 11, line 30, after "habitat", insert --of--.

Claim 6, column 12, line 18, change "use as claimed in" to --method of--.

Signed and Sealed this

Eighteenth Day of January, 1994

Attest:

BRUCE LEHMAN

Attesting Officer          Commissioner of Patents and Trademarks